(12) United States Patent
Cho et al.

(10) Patent No.: US 11,220,716 B2
(45) Date of Patent: Jan. 11, 2022

(54) METHODS FOR PREDICTING THE PROGNOSIS OF BREAST CANCER PATIENT

(71) Applicant: GENCURIX INC., Seoul (KR)

(72) Inventors: Sang Rae Cho, Seoul (KR); Young Ho Moon, Seoul (KR); Jin Il Han, Seoul (KR); Young Kee Shin, Seoul (KR)

(73) Assignee: GENCURIX INC., Seoul (KR)

( * ) Notice: Subject to any disclaimer, the term of this patent is extended or adjusted under 35 U.S.C. 154(b) by 786 days.

(21) Appl. No.: 15/938,633

(22) Filed: Mar. 28, 2018

(65) Prior Publication Data

US 2018/0216199 A1 Aug. 2, 2018

Related U.S. Application Data

(63) Continuation of application No. PCT/KR2017/013602, filed on Nov. 27, 2017.

(51) Int. Cl.
*C12Q 1/6886* (2018.01)
*C12Q 1/68* (2018.01)

(52) U.S. Cl.
CPC ............ *C12Q 1/6886* (2013.01); *C12Q 1/68* (2013.01); *C12Q 2600/118* (2013.01); *C12Q 2600/158* (2013.01)

(58) Field of Classification Search
CPC .. C12Q 1/6886; C12Q 1/68; C12Q 2600/118; C12Q 2600/158
See application file for complete search history.

(56) References Cited

U.S. PATENT DOCUMENTS

| | | | | |
|---|---|---|---|---|
| 10,655,187 | B2 * | 5/2020 | Shin | .............. C12Q 1/6886 |
| 2013/0344482 | A1 * | 12/2013 | Shin | ............ G01N 33/57415 |
| | | | | 435/6.11 |
| 2016/0102359 | A1 * | 4/2016 | Shin | .............. C12Q 1/6886 |
| | | | | 435/6.11 |

FOREIGN PATENT DOCUMENTS

| | | | |
|---|---|---|---|
| KR | 10-2012-0079295 A | 7/2012 | |
| KR | 10-2014-0125239 A | 10/2014 | |
| KR | 10-2014-0125647 A | 10/2014 | |
| WO | WO-2014171778 A1 * | 10/2014 | ......... C12Q 1/6886 |

OTHER PUBLICATIONS

BC Cancer Agency: Care & Research, "Breast Staging Diagram", (2003): 1-2. (Year: 2003).*
Filipits et al. (2011) ,"A new molecular predictor of distant recurrence in ER-positive, HER2-negative breast cancer adds independent information to conventional clinical risk factors",Clin Cancer Res 17(18): 6012-6020 (Year: 2011).*
International Search Report and Written Opinion in corresponding PCT Application No. PCT/KR2017/013602, dated Feb. 22, 2018.
Bernard, P.S. et al., "Real-time PCR Technology for Cancer Diagnostics"., Clinical Chemistry, 2002, vol. 48, No. 8, pp. 1178-1185.
Kwon, M. J. et al., "Identification of Novel Reference Genes Using Multiplatform Expression Data and Their Validation for Quantitative Gene Expression Analysis", PLOS One, Jul. 2009, vol. 4, No. 7, document No. e6162, pp. 1-15.
Goldhirsch Aron, et al., "Meeting Highlights: International Consensus Panel on the Treatment of Primary Breast Cancer", Journal of Clinical Oncology, vol. 19, No. 18, Sep. 15, 2001: pp. 3817-3827.
Cox, D. R., "Regression Models and Life-Tables", Journal of the Royal Statistical Society, Series B (Methodological), vol. 34, No. 2 (1972), pp. 187-220.
Gyungyub Gong, et al., A new molecular prognostic score for predicting the risk of distant metastasis in patients with HR+/HER2− early breast cancer, Scientific Reports | 7:45554 | DOI: 10.1038/srep45554, pp. 1-11, published: Mar. 28, 2017.
Extended European Search Report in corresponding European Application No. 17874456.1, dated Apr. 24, 2020.
Ensel Oh et al, "A prognostic model for lymph node-negative breast cancer patients based on the integration of proliferation and immunity", Breast Cancer Research and Treatment, Jun. 11, 2011, vol. 132, No. 2, pp. 499-509, XP035029108.
Sun Yijun et al, "Improved breast cancer prognosis through the combination of clinical and genetic markers", Bioinformatics, Jan. 1, 2007, vol. 23, No. 1, pp. 30-37, XP002472523.
Farzana Kabir Ahmad et al, "Toward Integrated Clinical and Gene-Expression Profiles for Breast Cancer Prognosis: A Review Paper", International Journal of Biometrics and Bioinformatics, Jan. 1, 2009, vol. 3, No. 4, pp. 31-47, XP055686521.
Gyungyub Gong et al, "A new molecular prognostic score for predicting the risk of distant metastasis in patients with HR+/HER2− early breast cancer", Scientific Reports, Apr. 1, 2017, vol. 7, No. 1, XP055686459.

* cited by examiner

*Primary Examiner* — Jehanne S Sitton
*Assistant Examiner* — Daniel W Nielsen
(74) *Attorney, Agent, or Firm* — Leason Ellis LLP

(57) ABSTRACT

The present invention relates to a method of predicting the effectiveness of chemotherapy in a breast cancer patient, and more particularly, to a method for predicting the effectiveness of chemotherapy by measuring the expression levels of genes for predicting prognosis of breast cancer and a standard gene in a biological sample obtained from the breast cancer patient, and a method for predicting the difference between a patient group having a high effectiveness of chemotherapy and a patient group having a low effectiveness of chemotherapy.
Therefore, the method of the present invention can accurately predict the effectiveness of chemotherapy for the breast cancer patient and can be used for the purpose of presenting clues about the direction of breast cancer treatment in the future.

8 Claims, 4 Drawing Sheets
(1 of 4 Drawing Sheet(s) Filed in Color)
Specification includes a Sequence Listing.

SEQUENCE LISTING

<160> NUMBER OF SEQ ID NOS: 27

<210> SEQ ID NO 1
<211> LENGTH: 19
<212> TYPE: DNA
<213> ORGANISM: Artificial Sequence
<220> FEATURE:
<223> OTHER INFORMATION: UBE2C forward primer

<400> SEQUENCE: 1
aaaaggctac agcaggagc                                            19

<210> SEQ ID NO 2
<211> LENGTH: 19
<212> TYPE: DNA
<213> ORGANISM: Artificial Sequence
<220> FEATURE:
<223> OTHER INFORMATION: UBE2C reverse primer

<400> SEQUENCE: 2
agctgctcca tggatggtc                                            19

<210> SEQ ID NO 3

```
<211> LENGTH: 24
<212> TYPE: DNA
<213> ORGANISM: Artificial Sequence
<220> FEATURE:
<223> OTHER INFORMATION: TOP2A forward primer

<400> SEQUENCE: 3
aagagtcatt ccacgaataa ccat                                          24

<210> SEQ ID NO 4
<211> LENGTH: 20
<212> TYPE: DNA
<213> ORGANISM: Artificial Sequence
<220> FEATURE:
<223> OTHER INFORMATION: TOP2A reverse primer

<400> SEQUENCE: 4
gagggcttcc ttcagtattt                                               20

<210> SEQ ID NO 5
<211> LENGTH: 18
<212> TYPE: DNA
<213> ORGANISM: Artificial Sequence
<220> FEATURE:
<223> OTHER INFORMATION: RRM2 forward primer

<400> SEQUENCE: 5
tgggaatccc tgaaaccc                                                 18

<210> SEQ ID NO 6
<211> LENGTH: 19
<212> TYPE: DNA
<213> ORGANISM: Artificial Sequence
<220> FEATURE:
<223> OTHER INFORMATION: RRM2 reverse primer

<400> SEQUENCE: 6
gaacttcttg gctaaatcg                                                19

<210> SEQ ID NO 7
<211> LENGTH: 21
<212> TYPE: DNA
<213> ORGANISM: Artificial Sequence
<220> FEATURE:
<223> OTHER INFORMATION: FOXM1 forward primer

<400> SEQUENCE: 7
aagcacattg ccaagccagg c                                             21

<210> SEQ ID NO 8
<211> LENGTH: 19
<212> TYPE: DNA
<213> ORGANISM: Artificial Sequence
<220> FEATURE:
<223> OTHER INFORMATION: FOXM1 reverse primer

<400> SEQUENCE: 8
cagggaaagg ttgtggcgg                                                19

<210> SEQ ID NO 9
<211> LENGTH: 21
<212> TYPE: DNA
<213> ORGANISM: Artificial Sequence
<220> FEATURE:
<223> OTHER INFORMATION: MKI67 forward primer

<400> SEQUENCE: 9
```

```
cagaatgaga gctcccagcc t                                              21

<210> SEQ ID NO 10
<211> LENGTH: 21
<212> TYPE: DNA
<213> ORGANISM: Artificial Sequence
<220> FEATURE:
<223> OTHER INFORMATION: MKI67 reverse primer

<400> SEQUENCE: 10
tgcatgagaa ccttcgcact c                                              21

<210> SEQ ID NO 11
<211> LENGTH: 18
<212> TYPE: DNA
<213> ORGANISM: Artificial Sequence
<220> FEATURE:
<223> OTHER INFORMATION: BTN3A2 forward primer

<400> SEQUENCE: 11
cttcaagcct ggtgagga                                                  18

<210> SEQ ID NO 12
<211> LENGTH: 21
<212> TYPE: DNA
<213> ORGANISM: Artificial Sequence
<220> FEATURE:
<223> OTHER INFORMATION: BTN3A2 reverse primer

<400> SEQUENCE: 12
ttttctgcag tctatttttc c                                              21

<210> SEQ ID NO 13
<211> LENGTH: 17
<212> TYPE: DNA
<213> ORGANISM: Artificial Sequence
<220> FEATURE:
<223> OTHER INFORMATION: CTBP1 forward primer

<400> SEQUENCE: 13
ccttgggcat catcgga                                                   17

<210> SEQ ID NO 14
<211> LENGTH: 18
<212> TYPE: DNA
<213> ORGANISM: Artificial Sequence
<220> FEATURE:
<223> OTHER INFORMATION: CTBP1 reverse primer

<400> SEQUENCE: 14
gttgaagccg aaggcctt                                                  18

<210> SEQ ID NO 15
<211> LENGTH: 22
<212> TYPE: DNA
<213> ORGANISM: Artificial Sequence
<220> FEATURE:
<223> OTHER INFORMATION: CUL1 forward primer

<400> SEQUENCE: 15
agtactgaat tcttgcagca ga                                             22

<210> SEQ ID NO 16
<211> LENGTH: 23
<212> TYPE: DNA
```

```
<213> ORGANISM: Artificial Sequence
<220> FEATURE:
<223> OTHER INFORMATION: CUL1 reverse primer

<400> SEQUENCE: 16
tcttcgttgt tcctcaagca gac                                          23

<210> SEQ ID NO 17
<211> LENGTH: 22
<212> TYPE: DNA
<213> ORGANISM: Artificial Sequence
<220> FEATURE:
<223> OTHER INFORMATION: UBQLN1 forward primer

<400> SEQUENCE: 17
gaaatcctca gcttcaagaa ca                                           22

<210> SEQ ID NO 18
<211> LENGTH: 22
<212> TYPE: DNA
<213> ORGANISM: Artificial Sequence
<220> FEATURE:
<223> OTHER INFORMATION: UBQLN1 reverse primer

<400> SEQUENCE: 18
tgacattgct gatagtgtat ca                                           22

<210> SEQ ID NO 19
<211> LENGTH: 8
<212> TYPE: DNA
<213> ORGANISM: Artificial Sequence
<220> FEATURE:
<223> OTHER INFORMATION: UBE2C UPL probe

<400> SEQUENCE: 19 gggaaggc                                                            8

<210> SEQ ID NO 20
<211> LENGTH: 8
<212> TYPE: DNA
<213> ORGANISM: Artificial Sequence
<220> FEATURE:
<223> OTHER INFORMATION: TOP2A UPL probe

<400> SEQUENCE: 20 gcctctga                                                            8

<210> SEQ ID NO 21
<211> LENGTH: 8
<212> TYPE: DNA
<213> ORGANISM: Artificial Sequence
<220> FEATURE:
<223> OTHER INFORMATION: RRM2 UPL probe

<400> SEQUENCE: 21 aaagccag                                                            8

<210> SEQ ID NO 22
<211> LENGTH: 8
<212> TYPE: DNA
<213> ORGANISM: Artificial Sequence
<220> FEATURE:
<223> OTHER INFORMATION: FOXM1 UPL probe

<400> SEQUENCE: 22 aggctgga                                                            8
```

```
<210> SEQ ID NO 23
<211> LENGTH: 8
<212> TYPE: DNA
<213> ORGANISM: Artificial Sequence
<220> FEATURE:
<223> OTHER INFORMATION: MKI67 UPL probe

<400> SEQUENCE: 23 gaggagag                                                              8

<210> SEQ ID NO 24
<211> LENGTH: 8
<212> TYPE: DNA
<213> ORGANISM: Artificial Sequence
<220> FEATURE:
<223> OTHER INFORMATION: BTN3A2 UPL probe

<400> SEQUENCE: 24 caaggtgg                                                              8

<210> SEQ ID NO 25
<211> LENGTH: 8
<212> TYPE: DNA
<213> ORGANISM: Artificial Sequence
<220> FEATURE:
<223> OTHER INFORMATION: CTBP1 UPL probe

<400> SEQUENCE: 25 gccccacg                                                              8

<210> SEQ ID NO 26
<211> LENGTH: 8
<212> TYPE: DNA
<213> ORGANISM: Artificial Sequence
<220> FEATURE:
<223> OTHER INFORMATION: CUL1 UPL probe

<400> SEQUENCE: 26 gcagaggc                                                              8

<210> SEQ ID NO 27
<211> LENGTH: 8
<212> TYPE: DNA
<213> ORGANISM: Artificial Sequence
<220> FEATURE:
<223> OTHER INFORMATION: UBQLN1 UPL probe

<400> SEQUENCE: 27 ttgggagc                                                              8
```

METHODS FOR PREDICTING THE PROGNOSIS OF BREAST CANCER PATIENT

CROSS-REFERENCE TO RELATED APPLICATIONS

The present application is a continuation-in-part of International Application No.: PCT/KR2017/013602, filed on Nov. 27, 2017, which claims priority to Korean Application No.: 10-2016-0158466, filed on Nov. 25, 2016, which are incorporated by reference in their entireties.

INCORPORATION BY REFERENCE OF SEQUENCE LISTING

A sequence listing created on Mar. 28, 2018 as the ASCII text file "10524_006678-US0_ST25" having a file size of 5.32 bytes, is incorporated herein by reference in its entirety.

TECHNICAL FIELD

The present invention relates to a method for predicting the prognosis of breast cancer, and more particularly to a method for predicting the prognosis of breast cancer, the method comprising steps of: (a) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2), an immune-related gene from the biological sample obtained from the breast cancer patient; (b) normalizing the mRNA expression level measured in the step (a); and (c) predicting the prognosis of breast cancer by a combination of the at least one proliferation-related gene and the immune-related gene normalized in the step (b), wherein the prognosis is predicted to be poor when the proliferation-related gene is over-expressed and the prognosis is predicted to be good when the immune-related gene is over-expressed.

BACKGROUND OF THE INVENTION

Breast cancer is the most common cancer in women and the second most deadly cancer. The prevalence of breast cancer in 2001 was 90-100 per 100,000 people in the United States and 50-70 per 100,000 people in Europe. The onset of this disease is increasing worldwide. Risk factors for breast cancer include race, age, mutations in the cancer suppressor genes BRCA-1, BRCA-2, and p53. Alcohol consumption, high fat diets, lack of exercise, exogenous postmenopausal hormone and ionizing radiation also increase the risk of breast cancer. The prognosis of breast cancer is worse in estrogen receptors and progesterone receptor negative breast cancers (ER– and PR–, respectively), large tumor size, result of a high grade cytologic diagnosis, and people under 35 years of age (Goldhirsch et al. J. Clin. Oncol. 19: 3817-27). Approximately 212,000 new invasive breast cancer cases and 58,000 new noninvasive breast cancer cases were estimated to be diagnosed in 2005 and 40,000 women were expected to die of breast cancer in 2005.

After surgery, current methods of treating breast cancer require additional adjuvant treatment to reduce future recurrence, such chemotherapy, antihormonal therapy, target therapy or radiotherapy. Breast cancer has different characteristics depending on the status of major receptor of breast cancer, and therefore, histological examination is performed to determine whether hormone receptors (ER and PR) are expressed or over-expressed, and to determine metastasis status and lymph node metastasis (positive or negative). And establishes the basis for further treatment. Although these clinical information is widely used as an indicator of treatment decision, the heterogeneity of the cancer is greater than the phenotype of the clinical indicator, such that the prognosis of all cancers cannot be judged, and its usefulness is also limited.

Meanwhile, breast cancer is generally divided into several major stages, depending on the degree of invasion and metastasis: early stage, local progressive stage, local persistent stage and metastasis stage. Early stage of breast cancer includes non-invasive breast cancers such as lobular carcinoma in situ ("LCIS") and ductile carcinoma in situ ("DCIS"). In general, breast cancer is graded according to the Tumor Node Metastasis ("TNM") proposed by the American Joint Committee on Cancer (AJCC Cancer Staging Manual, 6th Edition). The TNM classification system defines breast cancer in seven separate stages: 0, I, IIA, IIB, IIIA, IIIB and IV. The subtypes of step 0, I and step II are generally early stage breast cancer. Some subtypes of step II and step III are advanced breast cancer. Step IV generally refers to metastatic breast cancer.

The 5-year survival prognosis for the early stage breast cancer is generally more than 60%, but for the advanced breast cancer this figure drops to 40-60%. The 5-year survival rate for the metastatic breast cancer is typically only around 15%. The most common distant metastatic sites in breast cancer include the lung, liver, bone, lymph nodes, skin and central nervous system (brain). Once diagnosed with metastatic breast cancer, patients are expected to live on average 18-24 months. The treatment of metastatic breast cancer is almost impossible, and the treatment for this disease is essentially no more than a pain relief.

Although, 70-80% of patients with hormone receptor positive (estrogen receptor-positive and/or progesterone receptor-positive; ER+ and/or PR+), HER2– (human epidermal growth factor receptor negative), pN0 or pN1 with early breast cancer markers have little risk of long-term metastasis and cancer chemotherapy is not required (Paik, Tang et al., 2006). But, it is so difficult to distinguish breast cancer patients based on conventional breast cancer treatment guidelines that most of the patients are treated with chemotherapy and radiation therapy after surgery.

Therefore, it is necessary to clearly predict the future prognosis of cancer in early stage breast cancer patients, to choose the most appropriate treatment method at the moment, and to carefully observe the patient's condition to prepare for bad prognosis such as metastatic recurrence.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Technical Problem

Figure 1:
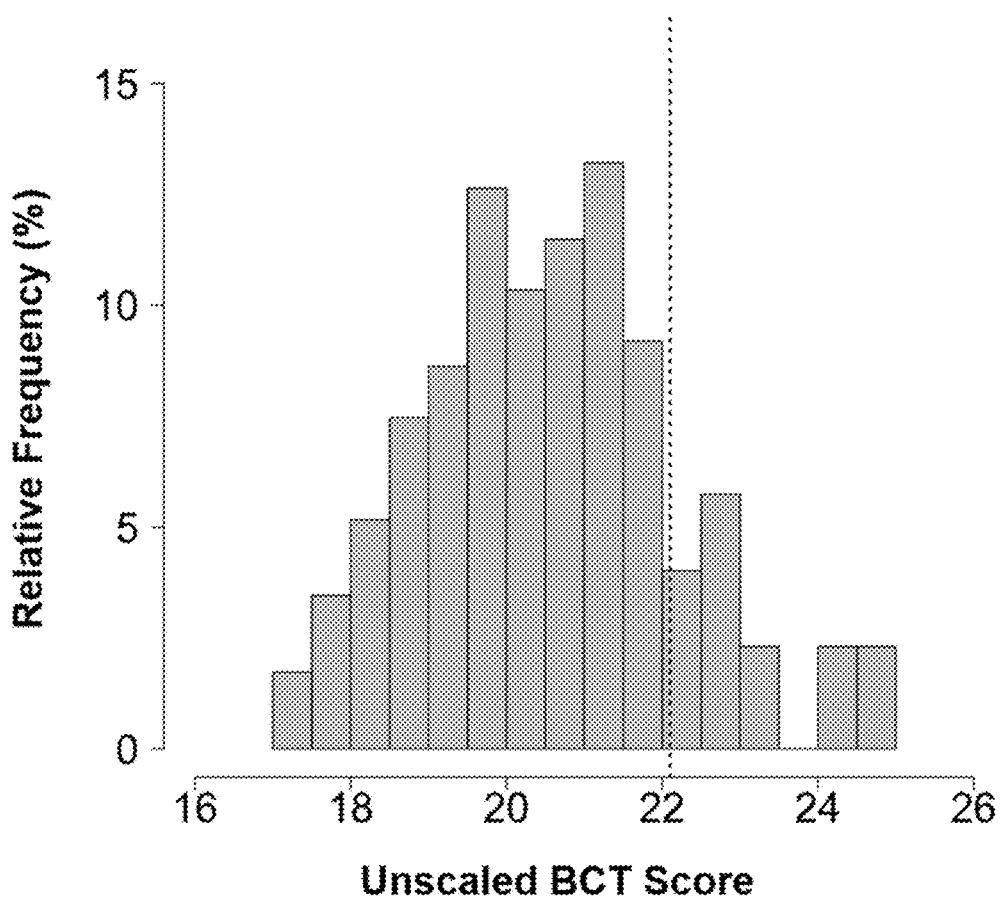
FIG. 1 shows the distribution of unscaled BCT scores in the algorithmic test group.

Early detection of breast cancer is on the rise due to the development of diagnostic techniques and increased routine screening. Early detection of breast cancer has increased the survival rate of breast cancer patients, but breast cancer recurrence rates of 5-20% are still reported. Therefore, detecting the risk of recurrence after treatment of early stage breast cancer is becoming an important factor in determining the follow-up treatment plan of breast cancer patients after initial treatment.

Accordingly, the present inventors have conducted extensive research to develop an algorithm for predicting the prognosis of breast cancer patients using FFPE samples containing cancer cells of patients, and they have developed a set of genes for predicting the prognosis after collecting and analyzing gene information and clinical information obtained from breast cancer. As a result, they have completed the present invention after they have confirmed the usefulness of the set of genes.

Accordingly, an aspect of the present invention is directed to provide a method for predicting the prognosis of breast cancer to provide information necessary for predicting the prognosis of a breast cancer patient, the method comprising the steps of:

(a) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2), an immune-related gene from the biological sample obtained from the breast cancer patient;

(b) normalizing the mRNA expression level measured in the step (a); and (c) predicting the prognosis of breast cancer by a combination of the at least one proliferation-related gene and the immune-related gene normalized in the step (b), wherein the prognosis is predicted to be poor when the proliferation-related gene is over-expressed and the prognosis is predicted to be good when the immune-related gene is over-expressed.

Another aspect of the present invention is to provide a method for predicting the prognosis of breast cancer to provide information necessary for predicting the prognosis of a breast cancer patient, the method comprising the steps of:

(a) measuring a mRNA expression level of UBE2C (Ubiquitin-conjugating enzyme E2C), TOP2A (Topoisomerase 2 alpha), RRM2 (ribonucleotide reductase M2), FOXM1 (Forkhead box M1) MKI67 (Marker of proliferation Ki-67) and a BTN3A2 (Butyrophilin subfamily 3 member A2) from a biological sample obtained from the breast cancer patient, respectively;

(b) normalizing the mRNA expression level measured in the step (a);

(c) evaluating the size of a tumor and a pN-stage in the breast cancer patient;

(d) calculating a numerical value by putting a normalized value obtained in the step (b), and the size of the tumor and the pN-stage in the step (c) into the following Equations 1 and 2

$$\text{Unscaled BCT score(U-BS)} = a^*\Delta Ct\_UBE2C + b^*\Delta Ct\_TOP2A + c^*\Delta Ct\_RRM2 + d^*\Delta Ct\_FOXM1 + e^*\Delta Ct\_MKI67 + f^*\Delta Ct\_BTN3A2 + g^*\text{Tumor\_size(cm)} + h^*\text{pN(0 or 1)} \quad \text{(Equation 1)}$$

BCT score=0 if 0.8*Unscaled BCT score(U-BS)−13.71<0

BCT score 0.8*U-BS−13.71

BCT score=10 if 0.8*U-BS−13.71>10     (Equation 2)

Wherein the value of the gene used for predicting the effectiveness of chemotherapy is a normalized mRNA expression value calculated using a standard gene; The tumor size is a value determined as the long axis length of the tumor and the pN is a value determined according to the pathological judgment of a lymph node metastasis, Wherein a is 0.16 to 1.09, b is 0 to 0.71, c is 0 to 0.53, d is 0 to 0.57, e is 0 to 0.35, f is −1.02 to 0, g is 0.25 to 1.52 and h is 0.19 to 2.25; and (e) predicting that the greater the value calculated in the step (d) is, the poorer the prognosis is.

Another aspect of the present invention is to provide a composition for predicting the prognosis of a breast cancer patient, the composition comprising agents for measuring the expression level of UBE2C, TOP2A, RRM2, FOXM1, MKI67 and BTN3A2 genes, respectively.

Another aspect of the present invention is to provide a composition for predicting the prognosis of a breast cancer patient, the composition consisting of agents for measuring the expression level of UBE2C, TOP2A, RRM2, FOXM1, MKI67 and BTN3A2 genes, respectively.

Still another aspect of the present invention is to provide a composition for predicting the prognosis of a breast cancer patient, the composition essentially consisting of agents for measuring the expression level of UBE2C, TOP2A, RRM2, FOXM1, MKI67 and BTN3A2 genes, respectively.

Still another aspect of the present invention is to provide a kit for predicting the prognosis of a breast cancer patient, the kit comprising agents for measuring the expression level of UBE2C, TOP2A, RRM2, FOXM1, MKI67 and BTN3A2 genes, respectively.

Still another aspect of the present invention is to provide use of agents for measuring the expression level of UBE2C, TOP2A, RRM2, FOXM1, MKI67 and BTN3A2 genes for preparing agents for predicting the prognosis of a breast cancer patient.

Technical Solution

An embodiment according to an aspect of the present invention provides a method for predicting the prognosis of breast cancer to provide information necessary for predicting the prognosis of a breast cancer patient, the method comprising the steps of:

(a) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2), an immune-related gene from the biological sample obtained from the breast cancer patient;

(b) normalizing the mRNA expression level measured in the step (a); and (c) predicting the prognosis of breast cancer by a combination of the at least one proliferation-related gene and the immune-related gene normalized in the step (b), wherein the prognosis is predicted to be poor when the proliferation-related gene is over-expressed and the prognosis is predicted to be good when the immune-related gene is over-expressed.

Another embodiment according to an aspect of the present invention provides a method for predicting the prognosis of breast cancer to provide information necessary for predicting the prognosis of a breast cancer patient, the method comprising the steps of:

(a) measuring a mRNA expression level of UBE2C (Ubiquitin-conjugating enzyme E2C), TOP2A (Topoisomerase 2 alpha), RRM2 (ribonucleotide reductase M2), FOXM1 (Forkhead box M1) MKI67 (Marker of proliferation Ki-67) and a BTN3A2 (Butyrophilin subfamily 3 member A2) from a biological sample obtained from the breast cancer patient, respectively;

(b) normalizing the mRNA expression level measured in the step (a);

(c) evaluating the size of a tumor and a pN-stage in the breast cancer patient;

(d) calculating a numerical value by putting a normalized value obtained in the step (b), and the size of the tumor and the pN-stage in the step (c) into the following Equations 1 and 2

$$\text{Unscaled BCT score(U-BS)} = a^*\Delta Ct\_UBE2C + b^*\Delta Ct\_TOP2A + c^*\Delta Ct\_RRM2 + d^*\Delta Ct\_FOXM1 + e^*\Delta Ct\_MKI67 + f^*\Delta Ct\_BTN3A2 + g^*\text{Tumor\_size(cm)} + h^*pN(0 \text{ or } 1) \quad \text{(Equation 1)}$$

BCT score=0 if 0.8*Unscaled BCT score(U-BS)−13.71<0

BCT score 0.8*U-BS−13.71

BCT score=10 if 0.8*U-BS−13.71>10   (Equation 2)

(Wherein the value of the gene used for predicting the effectiveness of chemotherapy is a normalized mRNA expression value calculated using a standard gene; The tumor size is a value determined as the long axis length of the tumor and the pN is a value determined according to the pathological judgment of a lymph node metastasis, Wherein a is 0.16 to 1.09, b is 0 to 0.71, c is 0 to 0.53, d is 0 to 0.57, e is 0 to 0.35, f is −1.02 to 0, g is 0.25 to 1.52 and h is 0.19 to 2.25; and (e) predicting that the greater the value calculated in the step (d) is, the poorer the prognosis is.

Another embodiment according to an aspect of the present invention provides a composition for predicting the prognosis of a breast cancer patient, the composition comprising agents for measuring the expression level of UBE2C, TOP2A, RRM2, FOXM1, MKI67 and BTN3A2 genes, respectively.

An embodiment according to another aspect of the present invention provides a composition for predicting the prognosis of a breast cancer patient, the composition consisting of agents for measuring the expression level of UBE2C, TOP2A, RRM2, FOXM1, MKI67 and BTN3A2 genes, respectively.

An embodiment according to still another aspect of the present invention provides a composition for predicting the prognosis of a breast cancer patient, the composition essentially consisting of agents for measuring the expression level of UBE2C, TOP2A, RRM2, FOXM1, MKI67 and BTN3A2 genes, respectively.

An embodiment according to another aspect of the present invention provides a kit for predicting the prognosis of a breast cancer patient, the kit comprising agents for measuring the expression level of UBE2C, TOP2A, RRM2, FOXM1, MKI67 and BTN3A2 genes, respectively.

An embodiment according to another aspect of the present invention provides a use of agents for measuring the expression level of UBE2C, TOP2A, RRM2, FOXM1, MKI67 and BTN3A2 genes for preparing agents for predicting the prognosis of a breast cancer patient.

Hereinafter, the present invention will be described in detail.

The present invention provides a method for predicting the prognosis of breast cancer to provide information necessary for predicting the prognosis of a breast cancer patient, the method comprising the steps of:

(a) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2), an immune-related gene from the biological sample obtained from the breast cancer patient;

(b) normalizing the mRNA expression level measured in the step (a); and (c) predicting the prognosis of breast cancer by a combination of the at least one proliferation-related gene and the immune-related gene normalized in the step (b), wherein the prognosis is predicted to be poor when the proliferation-related gene is over-expressed and the prognosis is predicted to be good when the immune-related gene is over-expressed.

The term "prognosis" in the present invention means progression of the disease during or after the treatment of breast cancer, and preferably means progression of disease after treatment, but is not limited thereto. The term "progression of the disease" as used herein refers to a concept including cancer cure, recurrence, metastasis or metastatic recurrence, and most preferably refers to metastatic recurrence, but is not limited thereto. The prognosis (or diagnosis of prognosis) of metastatic recurrence among these can provide clues to the direction of breast cancer treatment, especially because it can be used to determine in advance whether the tumor in the early stage breast cancer patient can develop into metastatic breast cancer in the future. This is a very meaningful task.

The "metastatic recurrence" in the present invention is a concept comprising local metastatic recurrence that occurs in breast cancer site before treatment and/or the ipsilateral breast and/or the contralateral breast, and the distant metastatic recurrence that occurs in distant areas such as the lung, liver, bone, lymph nodes, skin, and brain. Preferably, in the present invention, the metastatic recurrence may be distant metastatic recurrence, but is not limited to.

The term "metastasis" in the present invention means, after the initial treatment, that cancer cells derived and modified from at least one breast tumor continue to grow to be cancer at the site remote from the tumor (hereinafter referred to as "distant area"). The distant area may be, for example, in one or more lymph nodes, which may be mobile or fixed, ipsilateral or contralateral to the tumor, and the collarbone or underarm.

The prediction of the prognosis of breast cancer is mainly determined by the stage of disease after surgery to evaluate the size of the tumor (T), the metastasis to the periphery of the lymph nodes (N), and the distant metastasis (M) (TNM staging). The prediction of the prognosis in patients classified according to TNM stage is also different even in the same stage. Thus, the prediction of the prognosis in breast cancer of the same stage can be determined by expression of estrogen or progesterone receptor (ER or PR) and overexpression of HER2 (human epidermal growth factor receptor 2) or amplification of the gene. Even breast cancer of the same stage, the pathology and prognosis vary significantly depending on the expression of estrogen receptor, progesterone receptor or HER2, so it is necessary to clearly distinguish it and to set the treatment method specifically.

Therefore, recently, the characteristics of breast cancer were classified by gene and molecular biology (Table 1). According to the subtype, the outcome and prognosis of treatment are different, and it is used as an index for selection of surgical method or chemotherapy.

TABLE 1

Molecular biological subtype classification of breast cancer

| Subtype | Characterization | Frequency (%) |
| --- | --- | --- |
| Luminal A type | ER positive and/or PR positive<br>HER2 negative<br>Low expression of Ki67 | 30~70 |
| Luminal B type | ER positive and/or PR positive<br>HER2 positive<br>(or high expression of Ki67 and HER2 negative) | 10~20 |
| Triple negative type | ER negative<br>PR negative<br>HER2 negative | 15~20 |
| HER2 type | ER negative<br>PR negative<br>HER2 positive | 5~15 |

The breast cancer in the present invention is preferably an estrogen receptor and/or progesterone receptor-positive and HER2 negative breast cancer, and most preferably it can be a Luminal A type breast cancer, but is not limited thereto.

In the case of breast cancer, the higher the stage is, the more advanced the cancer is, and the prognosis is also not good. Breast cancer is divided into 0 to 4 stages. Breast cancer uses TNM staging system, and three factors are required to determine TNM staging. There is a T stage determined by the size and character of the cancer itself, an N stage determined by the degree of involvement of the lymph nodes, and an M stage determined by whether there is metastasis to other sites other than the breast. The pathological characteristics in each stage are summarized in Table 2 below.

TABLE 2

Pathologic classification of breast cancer according to TNM stage

| Classification | Detailed divisions |
| --- | --- |
| T stage | T0: No evidence of tumor<br>Tis: Intraepithelial cancer<br>T1: The maximum diameter of the chest is less than 2 cm |

TABLE 2-continued

Pathologic classification of breast cancer according to TNM stage

| Classification | Detailed divisions |
| --- | --- |
| | T2: The maximum diameter of the dose is greater than 2 cm but less than 5 cm<br>T3: The maximal straightness of the dose is greater than 5 cm |
| N stage | N0: No lymph node metastasis<br>N1: Number of metastatic lymph nodes is 1 to 3<br>N2: The number of metastatic lymph nodes is more than 4 but less than 9<br>N3: The number of lymph nodes is more than 10 |
| M stage | M0: No remote transition<br>M1: There is a remote transition |

In the present invention, the breast cancer is preferably an early stage breast cancer, more preferably a breast cancer corresponding to pN0 or pN1 stage, most preferably a breast cancer classified as 1 or 2 stage according to the TNM stage, but it is not limited to.

Hereinafter, each step of the method for predicting the effectiveness of chemotherapy for the breast cancer patient is described in detail.

(a) obtaining a biological sample from the breast cancer patient;

In the present invention, the biological sample may be a breast cancer tissue of the breast cancer patient. The breast cancer tissue may also contain some normal cells, preferably a formalin-fixed paraffin-embedded (FFPE) tissue, a fresh tissue, and a frozen tissue containing cancer cells of a patient, but is not limited thereto.

(b) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2) immune-related gene from the sample in the (a).

A predictive marker of the prognosis of breast cancer t in the present invention can be proliferation-related genes consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67) and a BTN3A2 (Butyrophilin subfamily 3 member A2), an immune-related gene. Each of these may be independently selected, but may be used to predict the effectiveness of chemotherapy in the breast cancer patient, preferably by a combination of two or more genes.

Each of the above genes may be a sequence of each gene or a synonym of each gene known in the art, preferably a sequence of each gene derived from a human, more preferably UBE2C (Gene ID: 11065), TOP2A (Gene ID: 7153), RRM2 (Gene ID: 6241), FOXM1 (Gene ID: 2305), MKI67 (Gene ID: 4288), BTN3A2 (Gene ID: 11118), but is not limited thereto.

Synonyms and sequences for each gene can be found in GenBank.

In the present invention, the mRNA expression level can be measured by any method performed in the art to measure the expression level of the gene. Preferably, the methods can be performed using a microarray, a polymerase chain reaction (PCR), RT-PCR (qRT-PCR), real-time PCR, northern blot, DNA chip and RNA chip, but are not limited thereto.

The measurement of the expression level of the gene of interest of the present invention is preferably a detection of the expression level of the gene of interest, more preferably the quantitative detection of the expression level of the gene of interest. In order to detect the expression level, mRNA isolation in the sample tissue and cDNA synthesis in the mRNA may be necessary. In order to isolate mRNA, a method of isolating RNA in a sample known in the art can be used. Preferably, the sample is an FFPE sample, and thus it may be a method of separating mRNA suitable for FFPE sample. As the cDNA synthesis process, a cDNA synthesis method known in the art using mRNA as a template can be used. Preferably, the expression level of the predictive marker of the effectiveness of chemotherapy in the breast cancer patient of the present invention is quantitative detection of mRNA expression in the FFPE sample. Therefore, it can be measured by the mRNA isolation method for FFPE samples and real time reverse transcription quantitative polymerase chain reaction (RT-qPCR).

In addition, measurement of the expression level of the gene of interest in the present invention can be performed according to a method known in the art, but can be measured by an optical quantitative analysis system using a probe labeled with a reporter fluorescent dye and/or a quencher fluorescent dye. The measurement may be performed by a commercially available equipment, for example, a system such as ABIPRISM 7700™ Sequence Detection System™, Roche Molecular Biochemicals Lightcycler, and software attached thereto. Such measurement data can be expressed as a measurement value or a threshold cycle (Ct or Cp).

The point at which the measured fluorescence value is recorded as the first statistically significant point is the threshold cycle. This indicates that the detection target appears in inverse proportion to the initial value existing as a template of the PCR reaction, so that when the value of the threshold cycle is smaller, targets to detect exist more quantitatively.

(c) normalizing the mRNA expression level measured in the (b);

The expression levels of the genes to be detected in the present invention may be different in expression amounts of overall genes or expression levels depending on the patient or the sample, so the normalization is required. The normalization is accomplished through differences in expression amounts or expression levels of genes that may indicate differences in basal expression amounts or expression levels. Preferably, it calculates a ratio of an average expression amount of one to three genes (or the average of these expression amounts when a plurality of genes are selected) in CTBP1 (C-terminal-binding protein 1), CUL1 (cullin 1) and UBQLN1 (Ubiquilin-1).

(d) predicting the prognosis of breast cancer by a combination of the at least one proliferation-related gene and the immune-related gene normalized in the step (b), wherein the prognosis is predicted to be poor when the proliferation-related gene is over-expressed and the prognosis is predicted to be good when the immune-related gene is over-expressed.

In the present invention, the term "poor prognosis" means that the probability of metastasis, recurrence or metastatic recurrence of cancer after treatment is high, and the term "good prognosis" means that the probability of metastasis, recurrence or metastatic recurrence of cancer after treatment is low. Preferably, the term "poor prognosis" means that the probability of metastasis, recurrence or metastatic recurrence of cancer within 10 years is high, and the term "good prognosis" means that the probability of metastasis, recurrence or metastatic recurrence of cancer within 10 years is low.

The term "10 years" refers to 10 years from the time point when the cancer is removed by surgery of patients with the primary breast cancer (i.e., the starting point of surgery).

In the present invention, the overexpression of the proliferation-related genes is closely related to the bad prognosis in the breast cancer patient. The overexpression of the above-mentioned immune-related gene is closely related to the good prognosis in the breast cancer patient. Therefore, the prognosis of breast cancer can be more accurately predicted by combining the expression pattern of the proliferation-related genes and the immune-related gene.

The gene combination of the present invention can be used to select patients who do not need additional chemotherapy after surgery for primary breast cancer. The target patient group of the gene combination in the present invention is preferably a group of patients who have not undergone any chemotherapy even before and after the surgery, and patients with "good prognosis" are less likely to develop metastasis, recurrence or metastatic recurrence within 10 years, so additional chemotherapy is not needed after surgery, but patients with "poor prognosis", there is a high incidence of metastasis, recurrence, or metastatic recurrence within 10 years after surgery, so additional chemotherapy may be recommended after surgery.

In the present invention, patients with the low effectiveness of chemotherapy are those who are predicted not to have a poor prognosis of the breast cancer patient (i.e., who are expected to have a "good prognosis" in the future) and do not require additional chemotherapy after surgery because of the low probability of metastasis, recurrence or metastatic recurrence within 10 years. However, patients with the high effectiveness of chemotherapy are those who are predicted to have a poor prognosis of the breast cancer patient (i.e., who are expected to have a "bad prognosis" in the future), and require additional chemotherapy after surgery because of the high probability of metastasis, recurrence or metastatic recurrence within 10 years. In other words, patients who are predicted not to have a bad prognosis of breast cancer can be determined to be more advantageous for the progression of breast cancer without the chemotherapy in the future because the side effects due to the chemotherapy are larger than the therapeutic effect. However, patients who are predicted to have a poor prognosis of the breast cancer patient can be determined to be more advantageous for the progression of breast cancer with the chemotherapy in the future because the therapeutic effect are larger than the side effects due to the chemotherapy.

In addition, the present invention further includes a step of evaluating the size and pN-stage of the tumor after the (b). In the (d), The present invention provides a method for predicting the prognosis of breast cancer, which is characterized that if the size of the tumor is larger and the pN stage is higher, it is determined that the prognosis is poor.

In other words, the prognosis of breast cancer can be more accurately predicted by combining the expression of the proliferation-related genes, the expression of the immune-related genes, the size of the tumor and the pN-stage, and the method for predicting the prognosis of breast cancer in the breast cancer patient through such a combination have not been reported in the past.

In the present invention, the size of the tumor refers to the length of the major axis of the cancer, preferably the length of the major axis of the cancer measured by a pathologist. The size of the tumor is expressed in centimeters.

In the present invention, the pN refers to a method of determining the metastasis to the lymph node by a pathological classification among the methods of classifying the stage of breast cancer. The method of the pathological classification is also called postsurgical histopathological classification. It is a method of distinguishing pathologic stages by collecting information from surgical or pathological examinations together with the information obtained before starting treatment in the breast cancer patient.

The pN is a method of discrimination based on the degree of metastasis to the lymph nodes. The axillary lymph nodes are resected to determine whether the tumor is metastasized. The higher the pN level is, the more metastasis of tumor cell to the lymph nodes has occurred. So the effectiveness of chemotherapy can be determined to be high because the prognosis of breast cancer was poor.

In the present invention, the pN may preferably be the pN0 or the pN1, but is not limited thereto. The pN0 refers to a stage where metastasis to the local lymph node is not observed. The pN1 refers a stage in which micrometastases in one to three ipsilateral axillary lymph nodes are found.

Therefore, by determining the size of the tumor and the pN stage as a prognostic predictor of the breast cancer patient together with the expression levels of the genes measured in the (b) according to the above method, the prognosis of the breast cancer patient can be more accurately predicted.

The present invention provides a method for predicting the prognosis of breast cancer to provide information necessary for predicting the prognosis of a breast cancer patient, the method comprising the steps of:

(a) measuring a mRNA expression level of UBE2C (Ubiquitin-conjugating enzyme E2C), TOP2A (Topoisomerase 2 alpha), RRM2 (ribonucleotide reductase M2), FOXM1 (Forkhead box M1) MKI67 (Marker of proliferation Ki-67) and a BTN3A2 (Butyrophilin subfamily 3 member A2) from a biological sample obtained from the breast cancer patient, respectively;

(b) normalizing the mRNA expression level measured in the step (a);

(c) evaluating the size of a tumor and a pN-stage in the breast cancer patient;

(d) calculating a numerical value by putting a normalized value obtained in the step (b), and the size of the tumor and the pN-stage in the step (c) into the following Equations 1 and 2

$$\text{Unscaled BCT score(U-BS)} = a*\Delta\text{Ct\_UBE2C} + b*\Delta\text{Ct\_TOP2A} + c*\Delta\text{Ct\_RRM2} + d*\Delta\text{Ct\_FOXM1} + e*\Delta\text{Ct\_MKI67} + f*\Delta\text{Ct\_BTN3A2} + g*\text{Tumor\_size(cm)} + h*\text{pN(0 or 1)} \quad \text{(Equation 1)}$$

BCT score=0 if 0.8*Unscaled BCT score(U-BS)−13.71<0

BCT score 0.8*U-BS−13.71

$$\text{BCT score} = 10 \text{ if } 0.8*\text{U-BS}-13.71 > 10 \quad \text{(Equation 2)}$$

Wherein the value of the gene used for predicting the effectiveness of chemotherapy is a normalized mRNA expression value calculated using a standard gene; The tumor size is a value determined as the long axis length of the tumor and the pN is a value determined according to the pathological judgment of a lymph node metastasis, Wherein a is 0.16 to 1.09, b is 0 to 0.71, c is 0 to 0.53, d is 0 to 0.57, e is 0 to 0.35, f is −1.02 to 0, g is 0.25 to 1.52 and h is 0.19 to 2.25; and (e) predicting that the greater the value calculated in the step (d) is, the poorer the prognosis is.

The (a) to (d) are the same as described above.

(e) calculating a numerical value by putting a normalized value obtained in the step (c), and the size of the tumor and the pN-stage in the step (d) into the following Equations 1 and 2

$$\text{Unscaled BCT score(U-BS)} = a*\Delta\text{Ct\_UBE2C} + b*\Delta\text{Ct\_TOP2A} + c*\Delta\text{Ct\_RRM2} + d*\Delta\text{Ct\_FOXM1} + e*\Delta\text{Ct\_MKI67} + f*\Delta\text{Ct\_BTN3A2} + g*\text{Tumor\_size(cm)} + h*\text{pN(0 or 1)} \quad \text{(Equation 1)}$$

BCT score=0 if 0.8*Unscaled BCT score(U-BS)−13.71<0

BCT score 0.8*U-BS−13.71

$$\text{BCT score} = 10 \text{ if } 0.8*\text{U-BS}-13.71 > 10 \quad \text{(Equation 2)}$$

Wherein the value of the gene used for predicting the effectiveness of chemotherapy is a normalized mRNA expression value calculated using a standard gene; The tumor size is a value determined as the long axis length of the tumor and the pN is a value determined according to the pathological judgment of a lymph node metastasis, Wherein a is 0.16 to 1.09, b is 0 to 0.71, c is 0 to 0.53, d is 0 to 0.57, e is 0 to 0.35, f is −1.02 to 0, g is 0.25 to 1.52 and h is 0.19 to 2.25;

The score of predicting prognosis is calculated by linear combination of the gene and the coefficient corresponding to each tumor size and pN. The proliferation gene, tumor size, and pN have a positive coefficient, and the immune gene has a negative coefficient. Each coefficient is applied within a 95% confidence interval of the calculated coefficient value (point estimate) as a result of the survival analysis, and preferably the point estimate of each coefficient is used.

| Coefficient | Point estimate | 95% confidence interval |
| --- | --- | --- |
| a (UBE2C) | 0.63 | 0.16~1.09 |
| b (TOP2A) | 0.32 | 0.00~0.71 |
| c (RRM2) | 0.13 | 0.00~0.53 |
| d (FOXM1) | 0.02 | 0.00~0.57 |
| e (MKI67) | 0.04 | 0.00~0.35 |
| f (BTN3A2) | −0.42 | −1.02~0.00 |
| g (Tumor size) | 0.89 | 0.25~1.52 |
| h (pN) | 1.22 | 0.19~2.25 |

Preferably, the method for predicting the prognosis of the breast cancer patient according to the present invention is related to the two major biological characteristics that govern the clinical outcome of the breast cancer patient, namely immune response and cell proliferation. Genes which were expressed stably in FFPE tissue specimens and shown large different expression according to prognosis were screened. The coefficients for the genes and two important clinical information (the tumor size and the pN stage) for prognosis were calculated by Cox analysis and the BCT score can be obtained by multiplying expression values of normalized genes, the tumor size and the pN stage according to the following Equation 1 to predict the prognosis of breast cancer.

$$\text{Unscaled BCT score} = 0.63*\Delta\text{Ct\_UBE2C} + 0.32*\Delta\text{Ct\_TOP2A} + 0.13*\Delta\text{Ct\_RRM2} + 0.02*\Delta\text{Ct\_FOXM1} + 0.04*\Delta\text{Ct\_MKI67} - 0.42*\Delta\text{Ct\_BTN3A2} + 0.89*\text{Tumor\_size(cm)} + 1.22*\text{pN(0 or 1)} \quad \text{(Equation 1)}$$

The degree to which the prognostic factors (genes, clinical information) affect the survival rate can be shown as a quantitative value by Cox proportional hazards analysis. The Cox proportional hazards model expresses the degree of the prognostic factors affecting the survival rate through the relative hazard ratio (HR), which is a proportion of the risk in the absence and in the presence of prognostic factors. If the value of the relative hazard ratio (HR) is greater than 1, the risk in the presence of prognostic factors is higher than that in the absence. If the prognostic factor is less than 1, the risk in the presence of prognostic factors is further reduced. The conversion of the relative hazard ratio to the log scale for each prognostic factor is called the coefficient for each factor and this value is used as the coefficient for calculating the BCT score model (Cox, David R. "Regression models and life-tables" Journal of the Royal Statistical Society. Series B (Methodological) (1972): 187-220). The coefficient of the gene was verified the validity of the result of the equation through cross validation.

In the above equation, a value obtained by normalizing the expression level of each gene is substituted into each 'ΔCt_prognosis prediction gene'. The normalization is accomplished through differences in expression amounts or expression levels of genes that may indicate differences in basal expression amounts or expression levels. Preferably, it calculates a ratio of an average expression amount of one to three genes (or the average of these expression amounts when a plurality of genes are selected) in CTBP1 (C-terminal-binding protein 1), CUL1 (cullin 1) and UBQLN1 (Ubiquilin-1).

Specifically, the value of "ΔCt-prognosis prediction gene" is a value obtained by adding 30 after the expression value of each prognostic gene was subtracted from the average expression value of the standard genes including CTBP1 (C-terminal-binding protein 1), CUL1 (cullin 1) and UBQLN1 (Ubiquilin-1) This value becomes a normalized value of each prognosis prediction gene. That is, the normalized value of each prognosis prediction gene is calculated by the following Equation:

ΔCt_prognosis prediction gene=((Ct_CTBP1+Ct_CUL1+Ct_UBQLN1)/3)−Ct_prognosis prediction gene+30

(The above-mentioned "prognosis prediction gene" refers to any one among UBE 2 C (Ubiquitin-conjugating enzyme E2C), TOP2A (Topoisomerase 2 alpha), RRM 2 (ribonucleotide reductase M2), FOXM 1 (Forkhead box M1), MKI 67 (Marker of proliferation Ki-67) and BTN3A2 (Butyrophilin subfamily 3 member A2).

The "Ct" refers to the number of cycles when a certain amount of PCR amplification product is amplified. In using the real-time RT-PCR method, since the change in the fluorescence intensity is generally equal to a noise level, which is equal to 0, when the number of amplification cycles is 1 to 10, such fluorescence intensity is regarded as a blank of the sample of the amplification product 0. A fluorescence value obtained by calculating the standard deviation SD thereof and multiplied by 10 is determined as a threshold value, and the number of PCR cycles first exceeding the threshold is regarded as a Ct (cycle threshold) value. Therefore, when the amplification product is large, the Ct value becomes a small value, and when the amplification product is small, the Ct value becomes a large value.

In the present invention, expression values of respective prognostic genes are normalized using standard genes, and the average Ct values of three standard genes are used to minimize technical errors that may occur in the test.

In the present invention, in order to express the calculated value of (Equation 1) as an intuitive numerical value, the calculated value is converted to a value between 0 and 10 by a linear transformation as shown in (Equation 2).

BCT score=0 if 0.8*Unscaled BCT score(U-BS)−13.71<0

BCT score=0.8*U-BS−13.71

BCT score=10 if 0.8*U-BS−13.71>10  (Equation 2)(BCT score calculation formula)

(f) predicting that the greater the numerical value calculated in the (e) is, the poorer the prognosis is:

According to one example of the present invention, in the method of predicting the prognosis of breast cancer according to the present invention, the point at which the sum of the sensitivity and the specificity as parameters for evaluating the accuracy of the risk group classification was maximized was calculated. As a result, we determined that when the numerical value calculated according to the above Equation 1 exceeded 22.1, the prognosis of breast cancer was poor (high risk of metastasis), and when the value is 22.1 or less, the prognosis of breast cancer (low risk of metastasis) was good.

Meanwhile, in the case of Equation 2 (BCT score) obtained by linear transformation of Equation 1 (Unscaled BCT score), we determined that if the value is 4 or larger, the prognosis of breast cancer was poor (metastatic high risk group) and if the value was less than 4, the prognosis of breast cancer (low risk of metastasis) was good.

In the present invention, the "sensitivity" refers to the percentage of high-risk patients in the test results of patients who have metastasized within 10 years, and the 'specificity' refers to the percentage of low risk patients in the test results of patients who do not have metastasized for 10 years.

According to one embodiment of the present invention, the inventors obtained the probability of distant metastatic recurrence in the algorithm calculation test group, and the result was that 10-year distant metastasis free survival rate was 97.85% in the low-risk group based on BCT score, and 1.07% in the high-risk group. That is, it was confirmed that there was statistically significant difference in the probability of distant metastatic recurrence (P-value=2.51e-11, log-rank test). And in the algorithm validation test group, 10-year distant metastasis free survival rate was 96.47% in the low-risk group based on BCT score, and 76.31% in the high-risk group. That is, there was statistically significant difference in the probability of distant metastatic recurrence the same as algorithm calculation test group (P-value=3.76e-05, log-rank test).

According to one embodiment of the present invention, the inventors analyzed using the Cox proportional hazards model to determine the statistical significance of the BCT score, and genes and clinical information used in the BCT score (i.e., cancer size and pN stage). As a result, the BCT score according to the present invention was confirmed to be more significant than the clinical information used as an index of general prognosis and the prognostic evaluation models such as NPI Score, PREDCIT and SNAP based on the clinical information.

According to another example of the present invention, the c-index of the BCT score and other models based on clinical information of the same patient group were compared. As a result, BCT score showed the highest c-index value, and it was confirmed that it showed higher prediction of breast cancer prognosis than other models.

Thus, the algorithm of the present invention can be used to screen patients who do not need additional chemotherapy after the primary breast cancer surgery. The subject group of the present algorithm of the present invention is preferably a group of patients who have not undergone any chemotherapy before and after surgery, and patients with a "good prognosis" have a low probability of metastasis, recurrence or metastatic recurrence within 10 years (low effectiveness of chemotherapy), but patients with 'poor prognosis' are more likely to develop metastasis, recurrence or metastatic recurrence within 10 years after surgery, and additional chemotherapy may be recommended (high effectiveness of chemotherapy) after surgery.

That is, the algorithm for predicting the effectiveness of chemotherapy of the breast cancer patient according to the above Equation 1 or Equation 1 and 2 of the present invention was obtained by analyzing proliferation-related genes, immune-related genes and clinical information (tumor size and pN stage) closely related to the prognosis of breast cancer from a wide range of clinical samples. The prediction of prognosis is greater than other models such as conventional prognostic evaluation model based on clinical information.

The present invention also provides a composition for predicting the prognosis of a breast cancer patient, the composition comprising agents for measuring the expression level of UBE2C, TOP2A, RRM2, FOXM1, MKI67 and BTN3A2 genes, respectively.

An embodiment according to another aspect of the present invention provides a composition for predicting the prognosis of a breast cancer patient, the composition consisting of agents for measuring the expression level of UBE2C, TOP2A, RRM2, FOXM1, MKI67 and BTN3A2 genes, respectively.

An embodiment according to still another aspect of the present invention provides a composition for predicting the prognosis of a breast cancer patient, the composition essentially consisting of agents for measuring the expression level of UBE2C, TOP2A, RRM2, FOXM1, MKI67 and BTN3A2 genes, respectively.

The present invention also provides a composition further comprises agents for measuring the expression level of CTBP1, CUL1 and UBQLN1 genes, respectively.

In the present invention, the agents for measuring the expression level of the genes may be a set of primer pair specifically binding to the UBE2C, TOP2A, RRM2, FOXM1, MKI67, BTN3A2, CTBP1, CUL1 and UBQLN1 genes.

As used herein, the term "primer" refers to an oligonucleotide which acts as a starting point for synthesis at conditions under which the synthesis of a primer extension product complementary to the nucleic acid chain (template) is induced, that is, a presence of polymerases such as a nucleotide and a DNA polymerase, and suitable temperature and pH.

Preferably, the primer is a deoxyribonucleotide and a single strand. The primers used in the present invention may comprise naturally occurring dNMPs (i.e., dAMP, dGMP, dCMP and dTMP), modified nucleotides or non-natural nucleotides. The primers may also include ribonucleotides.

The primer of the present invention may be an extension primer that is annealed to a target nucleic acid and forms a sequence complementary to the target nucleic acid by a template-dependent nucleic acid polymerase. It extends to a position where the immobilization probe is annealed and occupies the area where it is annealed.

The extension primer used in the present invention comprises a hybridization nucleotide sequence complementary to the first position of the target nucleic acid. The term "complementary" means that the primer or probe is sufficiently complementary to hybridize selectively to the target nucleic acid sequence under certain annealing or hybridization conditions, and is substantially complementary and perfectly complementary, and preferably means completely complementary. As used herein, the term "substantially complementary sequence" used in relation to a primer sequence is meant to include not only a completely matched sequence but also a sequence partially inconsistent with the sequence to be compared within a range that can anneal to a specific sequence and serve as a primer.

The primer should be long enough to prime the synthesis of the extension product in the presence of polymerases. The suitable length of the primer is determined by a number of factors, such as the temperature, the application, and the source of the primer, but is typically 15-30 nucleotides. Short primer molecules generally require lower temperatures to form a sufficiently stable hybrid complex with the template. The term "annealing" or "priming" means that the oligodeoxynucleotide or hexane has apposition to the template nucleic acid, and the opposition allows the polymerase to polymerize the nucleotides to form complementary nucleic acid molecules in the template nucleic acid or a portion thereof.

The sequence of the primer does not need to have a sequence completely complementary to a partial sequence of the template, and it is sufficient if the primer has sufficient complementarity within a range that hybridizes with the template and can perform the primer-specific action. Therefore, the primer in the present invention does not need to have a perfectly complementary sequence to the nucleotide sequence as a template, and it is sufficient if the primer has sufficient complementarity within a range capable of hybridizing to the gene sequence and acting as a primer. The design of such a primer can be easily carried out by those skilled in the art with reference to the nucleotide sequence described above, for example, by using a program for primer design (e.g., PRIMER 3 program).

Preferably, the primer pair in the present invention is characterized by being composed of the sequence shown in SEQ ID NO: 1 to SEQ ID NO: 18. The primers and probe sequences of the selected genes for measuring the expression level of the genes in the present invention are shown in Table 3 below.

TABLE 3

| Primer and probe sequence of gene for predicting prognosis of breast cancer | | | | |
| --- | --- | --- | --- | --- |
| Functional Classification | Gene | UPL probe | Forward primer | Reverse primer |
| Proliferation-related genes | UBE2C | SEQ ID NO: 19 GGGAAGGC | SEQ ID NO: 1 AAAAGGCTACAGCAGGAGC | SEQ ID NO: 2 AGCTGCTCCATGGATGGTC |

TABLE 3-continued

Primer and probe sequence of gene for predicting prognosis of breast cancer

| Functional Classification | Gene | UPL probe | Forward primer | Reverse primer |
|---|---|---|---|---|
| | TOP2A | SEQ ID NO: 20 GCCTCTGA | SEQ ID NO: 3 AAGAGTCATTCCACG AATAACCAT | SEQ ID NO: 4 GAGGGCTTCCTTCAG TATTT |
| | RRM2 | SEQ ID NO: 21 AAAGCCAG | SEQ ID NO: 5 TGGGAATCCCTGAAA CCC | SEQ ID NO: 6 GAACTTCTTGGCTAA ATCG |
| | FOXM1 | SEQ ID NO: 22 AGGCTGGA | SEQ ID NO: 7 AAGCACATTGCCAAG CCAGGC | SEQ ID NO: 8 CAGGGAAAGGTTGTG GCGG |
| | MKI67 | SEQ ID NO: 23 GAGGAGAG | SEQ ID NO: 9 CAGAATGAGAGCTCC CAGCCT | SEQ ID NO: 10 TGCATGAGAACCTTC GCACTC |
| Immune-related gene | BTN3A2 | SEQ ID NO: 24 CAAGGTGG | SEQ ID NO: 11 CTTCAAGCCTGGTGA GGA | SEQ ID NO: 12 TTTTCTGCAGTCTATT TTTCC |
| Standard genes | CTBP1 | SEQ ID NO: 25 GCCCCACG | SEQ ID NO: 13 CCTTGGGCATCATCGG A | SEQ ID NO: 14 GTTGAAGCCGAAGGC CTT |
| | CUL1 | SEQ ID NO: 26 GCAGAGGC | SEQ ID NO: 15 AGTACTGAATTCTTGC AGCAGA | SEQ ID NO: 16 TCTTCGTTGTTCCTCA AGCAGAC |
| | UBQLN1 | SEQ ID NO: 27 TTGGGAGC | SEQ ID NO: 17 GAAATCCTCAGCTTCA AGAACA | SEQ ID NO: 18 TGACATTGCTGATAGT GTATCA |

The present invention provides a kit for predicting the prognosis of a breast cancer patient, the kit comprising agents for measuring expression level of UBE2C, TOP2A, RRM2, FOXM1, MKI67 and BTN3A2 genes, respectively.

The present invention also provides a kit, wherein the kit further comprises agents for measuring expression level of the CTBP1, CUL1 and UBQLN1 genes, respectively.

The kit of the present invention may further comprise tools and/or reagents known in the art for use in RNA isolation and cDNA synthesis in PCR reaction reagents, in addition to a set of primer pair capable of amplifying the UBE2C, TOP2A, RRM2, FOXM1, MKI67, BTN3A2, CTBP1, CUL1 and UBQLN1 genes by PCR. The kit of the present invention may further comprise a tube, a well plate to be used for mixing the respective components and an instructional material describing the method of use, if necessary.

In addition, the present invention provides the use of agents for measuring expression level of UBE2C, TOP2A, RRM2, FOXM1, MKI67 and BTN3A2 genes for preparing agents for predicting the prognosis of a breast cancer patient.

The present invention also provides the use of agents, wherein the agents for measuring the expression level further comprises agents for measuring the expression level of CTBP1, CUL1 and UBQLN1 genes, respectively.

The "agents for measuring expression level of the genes" of the present invention is the same as described above, the "genes for preparing agents for predicting the prognosis" is the same as described above, and is one or more selected from the group consisting of UBE2C, TOP2A, RRM2, FOXM1, MKI67, BTN3A2, CTBP1, CUL1, and UBQLN1.

The term "comprising" of the present invention is used synonymously with "containing" or "characterized" and does not exclude additional component elements or method steps not mentioned in the composition or method. The term "consisting of" means excluding additional elements, steps or components not otherwise mentioned. The term "essentially consisting of" refers to comprising a component element or step which is described in the range of a composition or a method and which does not substantially affect its basic.

Advantageous Effect

The present invention relates to a gene group showing a significant correlation with the prognosis of breast cancer, and a method for predicting the prognosis of breast cancer using the gene group and clinical information. Therefore, the method of the present invention can accurately predict whether there is metastasis, recurrence or metastatic recurrence in breast cancer patients in the future, and can be used for the purpose of presenting clues about the direction of breast cancer treatment in the future.

Mode for Carrying Out Invention

Hereinafter, the present invention will be described in detail.

However, the following examples are illustrative of the present invention, and the present invention is not limited to the following examples.

Example 1

Collection of Expression Profiles of Early Breast Cancer Tissues

NCBI's Gene Expression Omnibus is a database site where researchers gather large-scale experimental data on gene expression and mutations, such as a microarray. The data on this site can be reanalyzed freely, and the process of deriving this prognostic gene also used data from this site.

The microarray data used in this study were limited to data using a microarray chip called 'Affymetrix Human Genome U133A Array'. There are about 22,000 probes on the chip, and each probe is a single gene. The degree of mRNA expression in most genes in the human body can be measured through the chip analysis.

In the NCBI GEO site, we examined microarray datasets for patients who were lymph node-negative patients and who were not treated with any chemotherapy after surgery. As a result, 684 specimen data from the following three datasets were obtained. The information on the sample dataset was shown in Tables 4 and 5 below.

TABLE 4

Sample Datasets

| GEO No. | GEO Registration year | Number of specimens | Specimen diagnosis (Date) | Retrospective observation period (Year) |
| --- | --- | --- | --- | --- |
| GSE2034 | 2005 | 286 | 1980-1995 | 7.17 |
| GSE7390 | 2006 | 198 | 1980-1998 | 12.01 |
| GSE11121 | 2008 | 200 | 1988-1998 | 7.54 |

TABLE 5

Pathological information of clinical samples

| | Discovery data set | | |
| --- | --- | --- | --- |
| Characteristics | GSE2034 | GSE7390 | GSE11121 |
| Total | 286 (100%) | 198 (100%) | 200 (100%) |
| Age | | | |
| ≤40 | 36 (13%) | 42 (21.2%) | 10 (5%) |
| 41-55 | 129 (45%) | 129 (65.2%) | 64 (32%) |
| 56-70 | 89 (31%) | 27 (13.6%) | 83 (42%) |
| ≥70 | 32 (11%) | | 43 (22%) |
| Not available | | | |
| ER status | | | |
| ER+ | 209 (73.1%) | 134 (67.7%) | 156 (78%) |
| ER− | 77 (26.9%) | 64 (32.3%) | 44 (22%) |
| Not available | | | |
| Grade | | | |
| G1 | 7 (2%) | 30 (15.2%) | 29 (14.5%) |
| G2 | 42 (15%) | 83 (41.9%) | 136 (68.0%) |
| G3 | 148 (52%) | 83 (41.9%) | 35 (17.5%) |
| Not available | 89 (31%) | 2 (1.0%) | |
| T stage | | | |
| T1 | 146 (51%) | 107 (54%) | 112 (56.0%) |
| T2 | 132 (46%) | 91 (46.0%) | 85 (42.5%) |
| T3 | 8 (3%) | | 3 (1.5%) |
| Not available | | | |
| N stage | | | |
| N− | 286 (100%) | 198 (100%) | 200 (100%) |
| N+ | | | |
| Not available | | | |

Example 2

According to the distribution of Distant-Metastasis-free survival (DMFS), patients without distant metastatic recurrence for more than 10 years were classified as 'good prognosis group' and those with distant metastatic recurrence within 5 years were classified as 'bad prognosis group'. As a result of classifying the sample groups according to these classification criteria, it was classified that good prognosis group was 212 and bad prognosis group was 159. The mean DMFS was 13 years in the good prognosis group and 2.2 years in the poor prognosis group.

Example 3

Selection of Gene for Predicting Prognosis

We examined the genes whose expression levels differed between the prognostic groups through SAM (Significant Analysis of Microarray) analysis on 212 samples with good prognosis and 159 samples with poor prognosis. Using the q-values of the SAM analysis results, we selected overexpressed genes in a good prognosis group and overexpressed genes in a poor prognosis group. The selected genes are combined into one set. As a result, a total of 302 non-redundant sets of genes were created, and a clustering analysis was performed by Principal Component Analysis (PCA) to determine the expression pattern of these genes. Gene Ontology (GO) function analysis was performed for each cluster in order to select the two major components and to explore the related biological functions for each major component.

The results of GO analysis showed that the main component 1 was concentrated in the proliferation and the main component 2 was concentrated in the immune response. Genes were selected with the highest expression level between prognostic groups in the genes belonging to two major components involved in proliferation and immune response. For each gene set, the gene was named p-gene representing the expression pattern of proliferation and i-gene representing the expression pattern of the immune response. In the gene group classified as the p-gene or the i-gene, genes meeting the following conditions were selected as candidate genes for the gene prognosis diagnostic model:

(i) high relevance to immunity or immune response.
(ii) large difference in expression between specimens.
(iii) high expression value on average.
(iv) high correlation of expression between FFPE and frozen specimens in qRT-PCR results.

The gene groups selected according to the above criteria are as follows.

(1) 10 kinds of proliferation-related gene groups (p-genes): AURKA, CCNB2, FOXM1, MKI67, MMP11, PTTG1, RACGAP1, RRM2, TOP2A and UBE2C (2) Six kinds of immune response-related genes (i-genes): BTN3A2, CCL19, CD2, CD52, HLA, DPA1 and TRBC1

Example 4

Selection of Variables for Implementing Algorithm Predicting Breast Cancer Prognosis 4-1. Obtaining Samples for Algorithm Implementation We obtained 174 samples of a breast cancer patient who were not treated with chemotherapy at Samsung Hospital and Asan Hospital, used them to implement the algorithm, and used 227 samples for algorithm verification.

Clinical information of the obtained patient samples is shown in Table 6 below.

TABLE 6

Clinical information of clinical specimen of Samsung and Asan hospitals

|  | Algorithm calculation test group | | Algorithm validation test group | |
|---|---|---|---|---|
|  | No. of patients | % | No. of Patients | % |
| Samples | 174 | 100.00% | 227 | 100.00% |
| Age (years) | | | | |
| <50 | 66 | 37.93% | 109 | 48.02% |
| >=50 | 108 | 62.07% | 113 | 49.78% |
| NA | 0 | 0.00% | 5 | 2.20% |
| pN | | | | |
| 0 | 163 | 93.68% | 208 | 91.63% |
| 1 | 11 | 6.32% | 19 | 8.37% |
| Tumor size (cm) | | | | |
| ≤2 | 141 | 81.03% | 189 | 83.26% |
| 2-5 | 33 | 18.97% | 38 | 16.74% |
| >5 | 0 | 0.00% | 0 | 0.00% |
| Pathologic Stage | | | | |
| IA | 136 | 78.16% | 177 | 77.97% |
| IIA | 31 | 17.82% | 34 | 14.98% |
| IIB | 7 | 4.02% | 11 | 4.85% |
| NA | 0 | 0.00% | 5 | 2.20% |
| Histologic Grade | | | | |
| 1 | 53 | 30.46% | 36 | 15.86% |
| 2 | 103 | 59.20% | 149 | 65.64% |
| 3 | 18 | 10.34% | 37 | 16.30% |

4-2. Selection of Genes to be Used for Prognosis Prediction

The RNAs of 16 genes previously selected were extracted from FFPE specimens and qRT-PCR was performed to calculate their expression values.

Changes in the risk of distant metastasis due to increased expression of each gene can be verified using the Cox proportional hazards model. The hazard ratio (HR) is defined as the ratio of the risk of occurrence of an event (distant metastasis) according to presence or absence of a risk factor (gene) in a Cox proportional hazards model at a certain time interval. If this risk is greater than 1, the risk factor will increase the risk of the event, but if less than 1 means that the risk will decrease.

The proliferation-related genes classified as p-genes had a risk value of 1 or more, and if the larger the expression value was, the worse the prognosis was. However, the genes classified as i-genes had a risk value of less than 1 and it was confirmed that the larger the expression value was, the better the result of the prognosis was.

The importance of predicting prognosis among the observed genes is higher than other genes, and the genes consistent with the direction of other studies and prognosis were selected as the genes to be used in the final algorithm.

The selected genes are five proliferation-related genes (UBE2C, TOP2A, MKI67, RRM2, and FOXM1) and one immune response-related gene (BTN3A2). Three additional standard genes (CTBP1, CUL1, and UBQLN1) suitable for FFPE tissue were selected from existing papers and their expression values were used for analysis ("Identification of novel reference genes using multiplatform expression data and their validation for quantitative gene expression analysis." PLoS One 4(7): e6162.2009).

4-3. Selection of Clinical Degree to Use in the Algorithm

Using the univariate Cox proportional hazards model, we identified the important clinical factors associated with metastatic recurrence in a breast cancer patient who were not treated with chemotherapy (p-value<0.05).

The results are shown in Table 7 below.

As shown in Table 7 below, pN, pathologic stage, tumor size and NPI score were found to be significant factors for distant metastasis.

TABLE 7

Significant clinical information for distant metastases through univariate Cox proportional hazards model

| | | All | | | Chemo | | | Non-chemo | | |
|---|---|---|---|---|---|---|---|---|---|---|
| | | HR | 95% CI | p-value | HR | 95% CI | p-value | HR | 95% CI | p-value |
| pN | 0 | 1.000 | | | 1.000 | | | 1.000 | | |
| | 1 | 3.732 | 2.418  5.761 | 0.000 | 2.602 | 1.624  4.168 | 0.000 | 14.832 | 4.819  45.650 | 0.000 |
| PT | 1 | 1.000 | | | 1.000 | | | 1.000 | | |
| | 2 | 1.888 | 1.217  2.928 | 0.005 | 1.302 | 0.806  2.102 | 0.281 | 4.668 | 1.568  13.900 | 0.006 |
| | 3 | 1.999 | 0.617  6.471 | 0.248 | 1.360 | 0.416  4.441 | 0.611 | — | —  — | — |
| Pathologic Stage | IA | 1.000 | | | 1.000 | | | 1.000 | | |
| | IIA | 2.473 | 1.479  4.136 | 0.001 | 1.592 | 0.902  2.810 | 0.108 | 5.750 | 1.663  19.880 | 0.006 |
| | IIB | 4.696 | 2.590  8.514 | 0.000 | 2.780 | 1.442  5.357 | 0.002 | 19.512 | 4.639  82.070 | 0.000 |
| | IIIA | 5.934 | 1.399  25.170 | 0.016 | 3.738 | 0.868  16.091 | 0.077 | — | —  — | — |
| Histologic Grade | 1 | 1.000 | | | 1.000 | | | 1.000 | | |
| | 2 | 1.982 | 1.029  3.818 | 0.041 | 1.771 | 0.830  3.778 | 0.140 | 1.607 | 0.416  6.214 | 0.492 |
| | 3 | 2.795 | 1.368  5.711 | 0.005 | 2.061 | 0.912  4.660 | 0.082 | 3.983 | 0.804  19.739 | 0.091 |
| Tumor Size | — | 1.271 | 1.121  1.441 | 0.000 | 1.131 | 0.969  1.321 | 0.119 | 4.579 | 2.275  9.217 | 0.000 |
| NPI | 1 | 1.000 | | | 1.000 | | | 1.000 | | |
| | 2 | 2.894 | 1.679  4.986 | 0.000 | 1.828 | 0.996  3.355 | 0.051 | 7.652 | 2.240  26.140 | 0.001 |
| | 3 | 4.257 | 2.415  7.507 | 0.000 | 2.650 | 1.436  4.893 | 0.002 | 12.233 | 2.236  66.930 | 0.004 |
| | 4 | — | —  — | — | — | —  — | — | — | —  — | — |
| NPI Score | — | 1.930 | 1.546  2.411 | 0.000 | 1.604 | 1.246  2.066 | 0.000 | 4.281 | 2.076  8.829 | 0.000 |
| Pathologic Stage | 1 | 1.000 | | | 1.000 | | | 1.000 | | |
| | 2 | 2.963 | 1.837  4.777 | 0.000 | 1.868 | 1.099  3.174 | 0.021 | 7.809 | 2.552  23.900 | 0.000 |
| | 3 | 5.920 | 1.396  25.112 | 0.016 | 3.729 | 0.866  16.057 | 0.077 | — | —  — | — |

TABLE 7-continued

Significant clinical information for distant metastases through univariate Cox proportional hazards model

| | | All | | | Chemo | | | Non-chemo | | |
|---|---|---|---|---|---|---|---|---|---|---|
| | HR | 95% CI | | p-value | HR | 95% CI | | p-value | HR | 95% CI | | p-value |
| Pathologic Stage | — | 2.802 1.836 | 4.275 | 0.000 | 1.8856 1.165 | 3.051 | 0.010 | 7.809 2.552 | 23.900 | 0.000 |
| Histologic Grade | — | 1.613 1.164 | 2.236 | 0.004 | 1.360 0.949 | 1.949 | 0.094 | 1.996 0.8522 | 4.673 | 0.111 |

Among these, tumor size was an important factor in distant metastatic recurrence in a breast cancer patient without chemotherapy, but not in a breast cancer patient who received chemotherapy.

The pN was significant in both patient groups without chemotherapy and with chemotherapy, but the hazard ratio values in patients without chemotherapy were seven times greater than those in chemically treated patients. In other words, the pN was found to be an index of more significant distant metastatic recurrence in patients who did not receive chemotherapy than patients who received chemotherapy.

The pathologic stage is also a significant factor but it is a concept that includes tumor size and pN. Because the NPI score is calculated based on the size of the cancer and the degree of lymph node metastasis, this index is also overlapped on the size of the cancer and the information on the pN. Finally, we selected tumor size and pN information for clinical information in a prognostic prediction model for patients who were not treated with chemotherapy.

Example 5

Derivation of the Equation of BCT Score Based on Cox Proportional Hazards Model 5-1. Derivation of the Equation The p-gene group (UBE2C, TOP2A, RRM2, FOXM1, and MKI67) of the proliferation-related genes shows a poor prognosis as the level of expression is increased, and the i-gene (BTN3A2) of the immune-related gene shows a good prognosis as the level of expression is increased. These genes were calculated by Cox proportional hazards analysis as follows.

Unscaled BCT score(U-BS)=0.63*ΔCt_UBE2C+
0.32*ΔCt_TOP2A+0.13*ΔCt_RRM2+
0.02*ΔCt_FOXM1+0.04*ΔCt_MKI67−
0.42*ΔCt_BTN3A2+0.89*Tumor_size(cm)+
1.22*pN(0 or 1)    (Equation of unscaled BCT score)

The Unscaled BCT score (U-BS) was calculated according to the above equation, and the distribution was confirmed. The results are shown in FIG. 1.

The cut-off of the BCT Score categorizes the patients as low risk or high risk for developing distant metastatic recurrence within 10 years. Evaluation variable of the accuracy of risk group classification is sensitivity and specificity. In the algorithm of the present invention, sensitivity and specificity are defined as follows.

Sensitivity: The percentage of high-risk patients who had a distant metastatic recurrence within 10 years.

Specificity: the percentage of low risk patients who did not have the distant metastatic recurrence within 10 years.

The larger the value of the sensitivity and specificity is, the better the classification is. However, increasing the sensitivity decreases the specificity, whereas increasing the specificity decreases the sensitivity. In the algorithm of the present invention, the BCT score classification point is calculated by calculating the cut-off point of the risk group classification so that the sum of the sensitivity and the specificity is maximized considering both the sensitivity and the specificity.

Figures 2A, 2B:
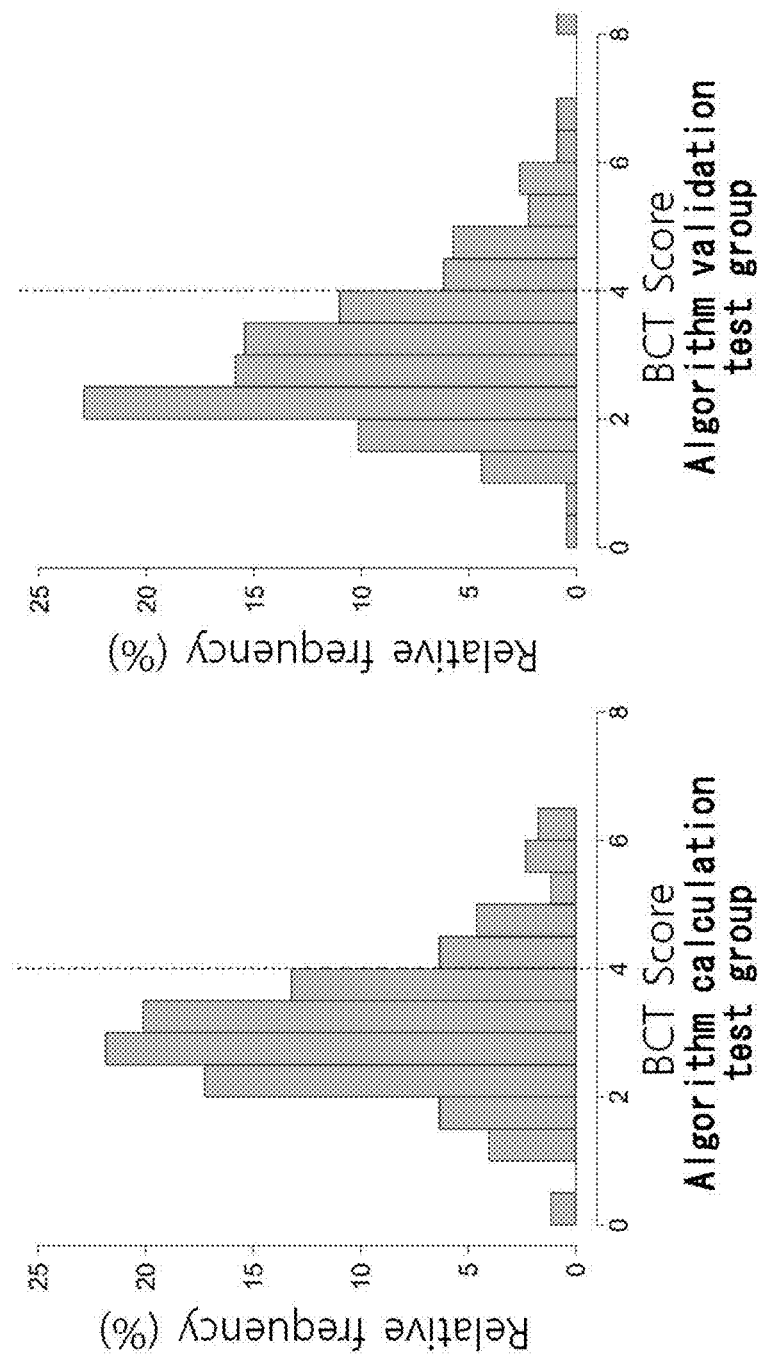
FIGS. 2A and 2B show the distribution of the BCT score in the algorithm calculation test group and the algorithm validation test group, respectively.

As shown in FIG. 2, the point at which the sum of the sensitivity and the specificity reaches a maximum according to the above criteria is 22.13767, which is designated as a threshold for distinguishing the high risk group from the low risk group. In other words, if the BCT score (BS) is 22.13767 or more, it can be classified as the high risk group of distant metastasis.

5-2. Derivation of Scaled Equation

In order to express the equation of the example <5-1> more intuitively, it was converted into a BCT score by linear transformation. The equation is as follows.

BCT score=0 if 0.8*U-BS−13.71<0

BCT score=0.8*U-BS−13.71

BCT score=10 if 0.8*
U-BS−13.71>10    (The equation of BCT score (BS))

If the value of BCT score is less than 0, it is replaced with 0, and if it is larger than 10, it is converted into 10. As the BCT score increases, the possibility of cancer recurrence, metastasis or metastatic recurrence within 10 years is increased.

Figure 3B:
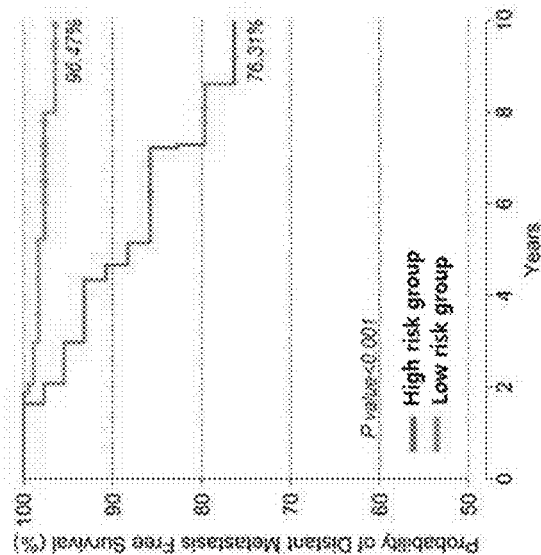
FIGS. 3A and 3B are graphs showing a distant metastasis-free survival in 10-year in the high risk group and the low risk group classified according to the BCT score in the algorithm calculation test group and the algorithm validation test group, respectively.
Figure 3A:
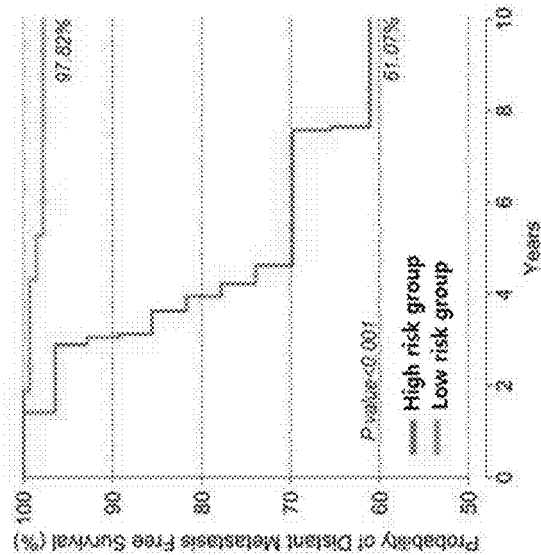

The BCT score was calculated according to the above equation and the distribution was confirmed. The results are shown in FIG. 2. As shown in FIG. 3, the threshold for classifying the patients in the high risk group and the low risk group for the distant metastasis was set to 4 (the point where the sum of the sensitivity and the specificity reached a maximum) in the BCT score. If the BCT score is 4 or more, it can be classified as high risk group with a recurrence, metastasis or metastatic recurrence and less than 4, it can be classified as low risk group.

Example 6

Performance Evaluation of Predicting Prognosis 6-1. Performance Evaluation Through Algorithm Calculation Test Group and Verification Test Group The high risk group classified according to the equation of Example 5 means that the recurrence, metastasis or metastatic recurrence may occur with a higher probability than the low risk group. FIG. 3 shows the results of estimation of distant metastasis recurrence probability through survival analysis of the algorithm calculation test group (discovery set) and the algorithm validation test group (validation set).

As shown in FIG. 3, the distant metastasis-free survival within 10 years in the low risk group based on the BCT score were 97.82% and 96.47% in the algorithm calculation test group and the algorithm validation test group, respectively. The distant metastasis-free survival within 10 years in the high risk group was 61.07% and 76.31%, respectively (p-values<0.001, log-rank test), indicating that there was a statistically significant difference in the distant metastasis free survival within 10 years in both test groups.

6-2. Statistical Significance Verification for Predicting Prognosis of BCT Score Using Univariate and Multivariate Cox Proportional Hazards Model To verify statistical significance for the prediction of distant metastasis of BCT score, we used the Cox proportional hazards analysis to determine whether it was more significant than clinical information and prognostic evaluation model based on clinical information.

As a result of the multivariate Cox proportional hazards analysis in the calculation test group and the verification test group of algorithms, the BCT score was confirmed to be a statistically significant index (p-values<0.05) in predicting distant metastasis compared with the general clinical information used as an index of prognosis.

Similarly, the BCT Score is a statistically significant indicator compared with the prognostic model based on clinical information and can be confirmed by multivariate Cox proportional hazards analysis (p-values<0.05).

TABLE 8

Multivariate Cox proportional hazards analysis of clinical information and prognostic prediction models

| | Algorithm calculation test group | | | Algorithm validation test group | | |
|---|---|---|---|---|---|---|
| | HR | 95% C.I. | P value | HR | 95% C.I. | P value |
| BCT Score | 2.22 | (1.08-4.58) | 0.030 | 1.88 | (1.10-3.21) | 0.022 |
| Age at surgery | 1.02 | (0.98-1.07) | 0.364 | 1.04 | (0.98-1.10) | 0.184 |
| Tumor Size | 1.50 | (0.47-4.74) | 0.494 | 0.79 | (0.33-1.89) | 0.597 |
| No. of LN metastasis | 1.53 | (0.77-3.04) | 0.220 | 0.17 | (0.02-1.42) | 0.103 |
| Histologic Grade | 1.36 | (0.50-3.69) | 0.543 | 1.51 | (0.54-4.27) | 0.435 |
| BCT Score | 2.54 | (1.35-4.78) | 0.004 | 2.02 | (1.17-3.50) | 0.012 |
| NPI Score | 1.76 | (0.42-7.36) | 0.437 | 1.43 | (0.37-5.48) | 0.600 |

TABLE 8-continued

Multivariate Cox proportional hazards analysis of clinical information and prognostic prediction models

| | Algorithm calculation test group | | | Algorithm validation test group | | |
|---|---|---|---|---|---|---|
| | HR | 95% C.I. | P value | HR | 95% C.I. | P value |
| PREDICT | 1.05 | (0.99-1.12) | 0.090 | 0.98 | (0.88-1.10) | 0.763 |
| SNAP | 0.93 | (0.74-1.18) | 0.545 | 0.91 | (0.71-1.16) | 0.438 |

6-3. Evaluation of Predictive Performance of Prognosis on of BCT Score Using C-Index The C-index has a value from 0.5 to 1. When the C-index is closer to the value of 0.5, the predictive possibility of prognosis is decreased, and when it is closer to 1, the predictive possibility of prognosis is increased. To evaluate the predictive possibility of prognosis of the BCT score, a clinical information-based model and a C-index comparative evaluation were performed.

Figure 4A:
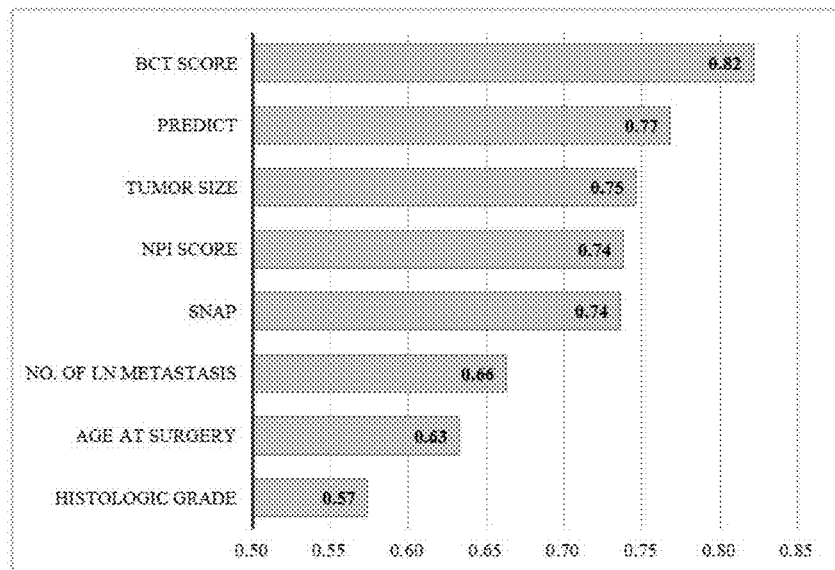
FIGS. 4A and 4B are graphs showing the results of the prediction performance evaluation of the prediction models of breast cancer prognosis through C-index in the algorithm calculation test group and the algorithm validation test group, respectively.
Figure 4B:
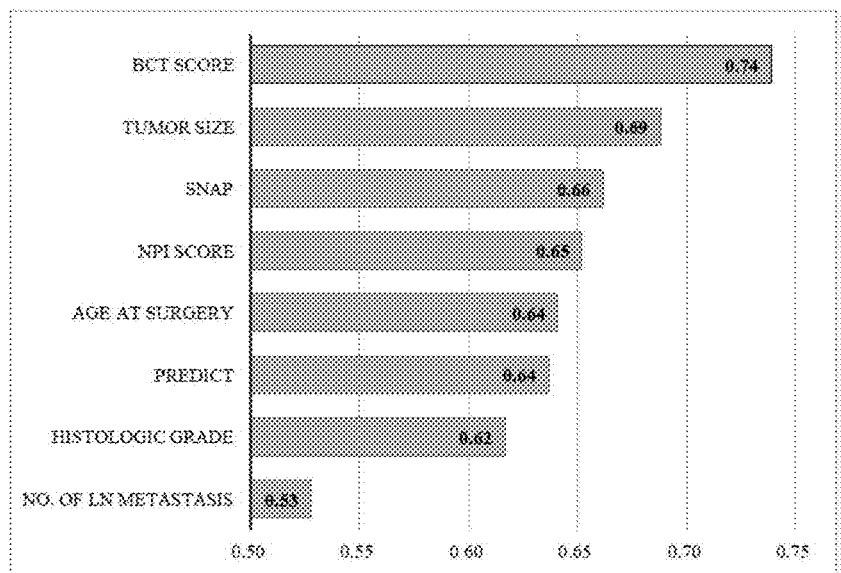

The c-index of the BCT score and other clinical information-based models were compared in the same patient group. As a result, BCT score showed the highest c-index value. This means that the BCT score had a higher predictive performance of prognosis than the other models of predicting prognosis (FIG. 4).

INDUSTRIAL APPLICABILITY

The present invention relates to the method for predicting the prognosis of breast cancer using 2 groups of genes which are significantly related to the prognosis of breast cancer, and the method of the present invention can accurately predict whether there is metastasis, recurrence or metastatic recurrence in breast cancer patients in the future. In particular, the method of the present invention can accurately predict the prognosis of HER2 type breast cancer which has very poor prognosis. Therefore, it can be used for the purpose of presenting information on the direction of breast cancer treatment in the future, and is highly available in industry

What is claimed is:

1. A method for treating breast cancer in a breast cancer patient, the method comprising the steps of:
   (a) collecting a biological sample from the breast cancer patient;
   (b) isolating mRNA from the biological sample from the breast cancer patient;
   (c) measuring mRNA expression level of a set of proliferation-related genes and an immune related gene from the biological sample wherein the set of proliferation-related genes and an immune related gene consists of:
      (i) UBE2C (Ubiquitin-conjugating enzyme E2C), TOP2A (Topoisomerase 2 alpha), MKI67 (Marker of proliferation Ki-67) and BTN3A2 (Butyrophilin subfamily 3 member A2);
      (ii) RRM2 (ribonucleotide reductase M2), FOXM1 (Forkhead box M1), MKI67 (Marker of proliferation Ki-67), and BTN3A2 (Butyrophilin subfamily 3 member A2); or
      (iii) UBE2C (Ubiquitin-conjugating enzyme E2C), TOP2A (Topoisomerase 2 alpha), RRM2 (ribonucleotide reductase M2), FOXM1 (Forkhead box M1), MKI67 (Marker of proliferation Ki-67) and BTN3A2 (Butyrophilin subfamily 3 member A2);
   (d) normalizing the mRNA expression level measured in step (c) to determine a normalized value of the mRNA expression level;
   (e) detecting in the biological sample an increase in a combination of normalized values of the proliferation-related genes compared to a reference breast tumor and/or a decrease in a normalized value of the immune-related gene compared to a reference breast tumor;

(f) diagnosing the breast cancer patient who has an increase in a combination of normalized values of the proliferation-related genes compared to a reference breast tumor and/or a decrease in normalized value of the immune-related gene compared to a reference breast tumor as requiring treatment; and (g) treating the diagnosed breast cancer patient by administering at least one of an anti-cancer agent, a surgery, and a radiation therapy.

2. The method of claim 1, wherein the breast cancer patient diagnosed as requiring treatment is the breast cancer patient having any one or more selected from the group consisting of recurrence, metastasis and metastatic recurrence of breast cancer.

3. The method of claim 1, wherein the breast cancer is a breast cancer which is an estrogen receptor-positive, a progesterone receptor-positive, or an estrogen receptor and progesterone receptor-positive, while being HER2-negative.

4. The method of claim 1, wherein the breast cancer is an early stage breast cancer classified as stage 1 or stage 2 according to the Tumor Node Metastasis (TNM) system.

5. The method of claim 1, wherein the method further comprises the step of evaluating the size of a tumor and a pN-stage after measuring the mRNA expression levels of the set of proliferation-related genes and an immune related gene from the biological sample in step (c), and when the size of the tumor is larger compared to the reference breast tumor and/or the pN-stage is higher compared to the reference breast tumor, then the breast cancer patient is diagnosed as requiring treatment.

6. The method of claim 1, wherein the step of normalizing comprises calculating a ratio against an average expression level of one or more selected standard genes in a group consisting of CTBP1 (C-terminal-binding protein 1), CUL1 (cullin 1) and UBQLN1 (Ubiquilin-1).

7. The method of claim 1, wherein the biological sample collected from the breast cancer patient is selected from the group consisting of a formalin-fixed paraffin-embedded (FFPE) tissue, a fresh tissue, and a frozen tissue containing cancer cells of the patient.

8. The method of claim 1, wherein the expression level of the gene is measured by a method selected from the group consisting of a microarray, a polymerase chain reaction (PCR), a RT-PCR, a quantitative RT-PCR (qRT-PCR), real-time PCR, northern blot, DNA chip, and RNA chip.

* * * * *